(12) United States Patent
Greiner-Perth

(10) Patent No.: US 9,352,348 B2
(45) Date of Patent: May 31, 2016

(54) DISPENSER WITH CHILD-PROOF LOCK

(71) Applicant: Juergen Greiner-Perth, Gottmadingen (DE)

(72) Inventor: Juergen Greiner-Perth, Gottmadingen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 31 days.

(21) Appl. No.: 14/032,590

(22) Filed: Sep. 20, 2013

(65) Prior Publication Data

US 2014/0097207 A1    Apr. 10, 2014

(30) Foreign Application Priority Data

Oct. 10, 2012 (DE) .......................... 10 2012 218 434

(51) Int. Cl.
*B05B 11/00* (2006.01)
*A61M 15/08* (2006.01)

(52) U.S. Cl.
CPC ......... *B05B 11/3059* (2013.01); *B05B 11/0027* (2013.01); *B05B 11/0032* (2013.01); *A61M 15/08* (2013.01); *A61M 2202/064* (2013.01); *A61M 2205/276* (2013.01)

(58) Field of Classification Search
CPC ............ B05B 11/0027; B05B 11/3059; B05B 11/306; B05B 11/032; B05B 11/3091; B05B 11/3091
USPC ............. 222/153.01, 153.09, 153.11, 153.13, 222/153.14
See application file for complete search history.

(56) References Cited

U.S. PATENT DOCUMENTS

| 3,770,168 A | | 11/1973 | Sagarin | |
|---|---|---|---|---|
| 4,353,483 A | * | 10/1982 | Pehr | ......................... 222/153.02 |
| 4,368,830 A | | 1/1983 | Soughers | |

(Continued)

FOREIGN PATENT DOCUMENTS

| DE | 33 42 883 A1 | 6/1985 |
|---|---|---|
| DE | 10 2004 021 668 A1 | 12/2005 |

(Continued)

OTHER PUBLICATIONS

Office Action of German Patent Office issued in German Application No. 10 2012 218 434.1 dated Feb. 15, 2013 (6 pages).

(Continued)

*Primary Examiner* — Daniel R Shearer
(74) *Attorney, Agent, or Firm* — Flynn, Thiel, Boutell & Tanis, P.C.

(57) ABSTRACT

A dispenser including a medium reservoir, a discharge opening, and a feeding device for feeding medium from the medium reservoir to the discharge opening, wherein an actuating handle is displaceable relative to the medium reservoir in an actuation direction to discharge medium.

The dispenser includes a protective device with two partial shells interconnected in a protective condition by a coupling device for repeated decoupling and coupling wherein the protective device is attachable to the feeding device in a protective position such that in the protective condition the accessibility and/or maneuverability of the actuating handle is prevented, and upon releasing the coupling device an enable condition of the protective device is achievable in which the partial shells are displaceable relative to another so that the protective device is removable from the feeding device, and thus accessibility or maneuverability of the actuating handle is obtainable thereby.

18 Claims, 5 Drawing Sheets

(56) References Cited

U.S. PATENT DOCUMENTS

| | | | | |
|---|---|---|---|---|
| 4,479,589 A | * | 10/1984 | Ford | 222/153.13 |
| 4,944,429 A | * | 7/1990 | Bishop | B05B 11/0027 222/153.13 |
| 5,657,905 A | * | 8/1997 | Glynn | 222/153.1 |
| 6,173,868 B1 | * | 1/2001 | DeJonge | A61M 15/0065 222/153.13 |
| 7,044,339 B1 | * | 5/2006 | Kuo | B05B 11/3059 222/182 |
| 7,757,901 B2 | * | 7/2010 | Welp | B05B 11/0032 222/153.13 |
| 8,336,739 B2 | * | 12/2012 | Margheritis | A61M 15/0065 222/153.06 |
| 8,544,694 B2 | * | 10/2013 | Waitz | 222/153.1 |
| 8,662,353 B2 | * | 3/2014 | Santoni | B05B 11/0008 222/182 |
| 8,939,323 B2 | * | 1/2015 | Knight | A61M 11/00 222/153.13 |
| 2003/0106901 A1 | | 6/2003 | Meshberg | |
| 2007/0080174 A1 | | 4/2007 | Coe et al. | |
| 2007/0262090 A1 | | 11/2007 | Ritsche | |
| 2008/0245896 A1 | | 10/2008 | Welp | |
| 2009/0242502 A1 | | 10/2009 | Qin | |
| 2009/0255958 A1 | | 10/2009 | Santoni et al. | |
| 2010/0018997 A1 | * | 1/2010 | Faneca Llesera | B05B 11/0027 222/153.06 |
| 2011/0088692 A1 | | 4/2011 | Auerbach et al. | |

FOREIGN PATENT DOCUMENTS

| | | |
|---|---|---|
| DE | 10 2004 023 528 A1 | 12/2005 |
| DE | 10 2004 050 679 A1 | 4/2006 |
| DE | 10 2009 049 903 A1 | 4/2011 |
| DE | 10 2010 011 761 A1 | 9/2011 |
| FR | 2 876 676 A1 | 4/2006 |
| JP | 2010195469 A * | 9/2010 |
| WO | WO 2005/107955 A1 | 11/2005 |
| WO | WO 2012/103740 A1 | 8/2012 |

OTHER PUBLICATIONS

European Patent Office Search Report issued in Application No. 13184893.9 with English translation of category of cited documents dated May 9, 2014 (8 pages).

European Search Report of European Patent Office issued in European Application No. EP 13 18 4893 with English translation of category of cited documents dated Aug. 6, 2014 (14 pages).

* cited by examiner

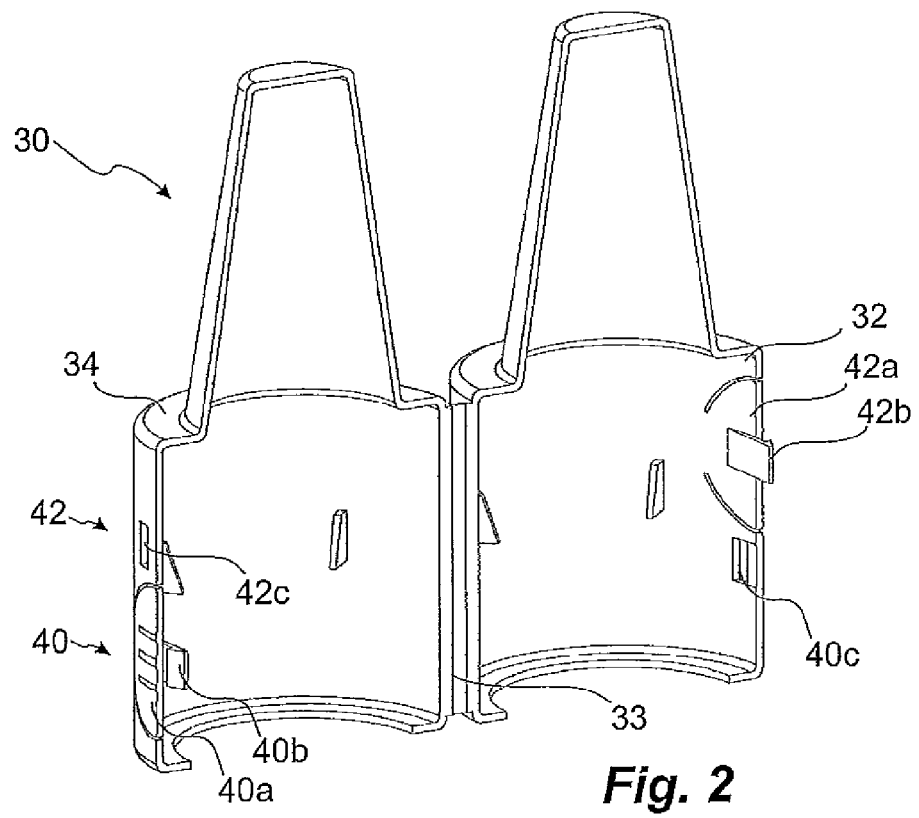
*Fig. 2*
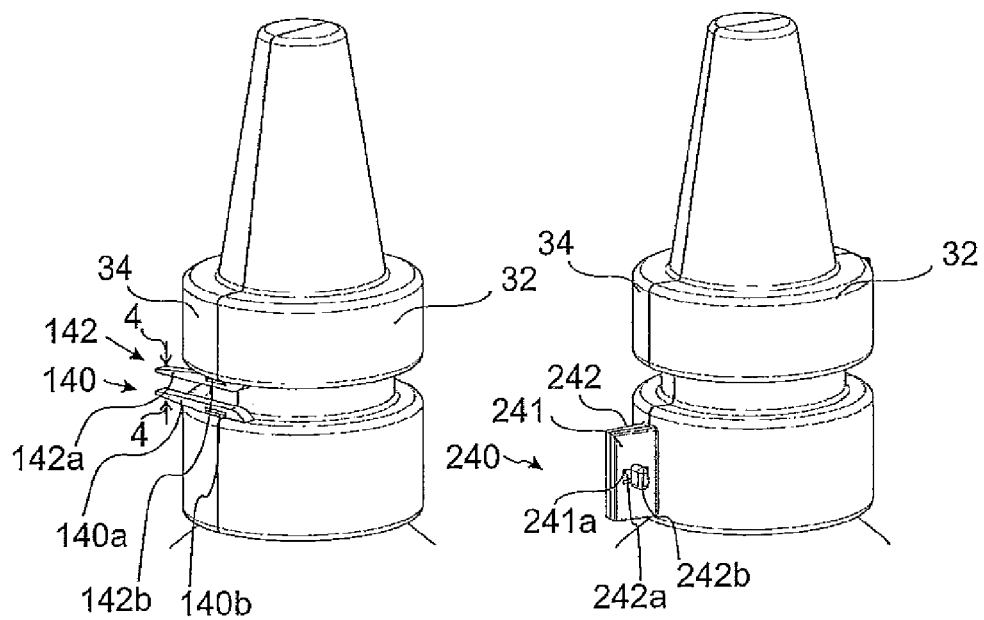
*Fig. 3a*  *Fig. 3b*

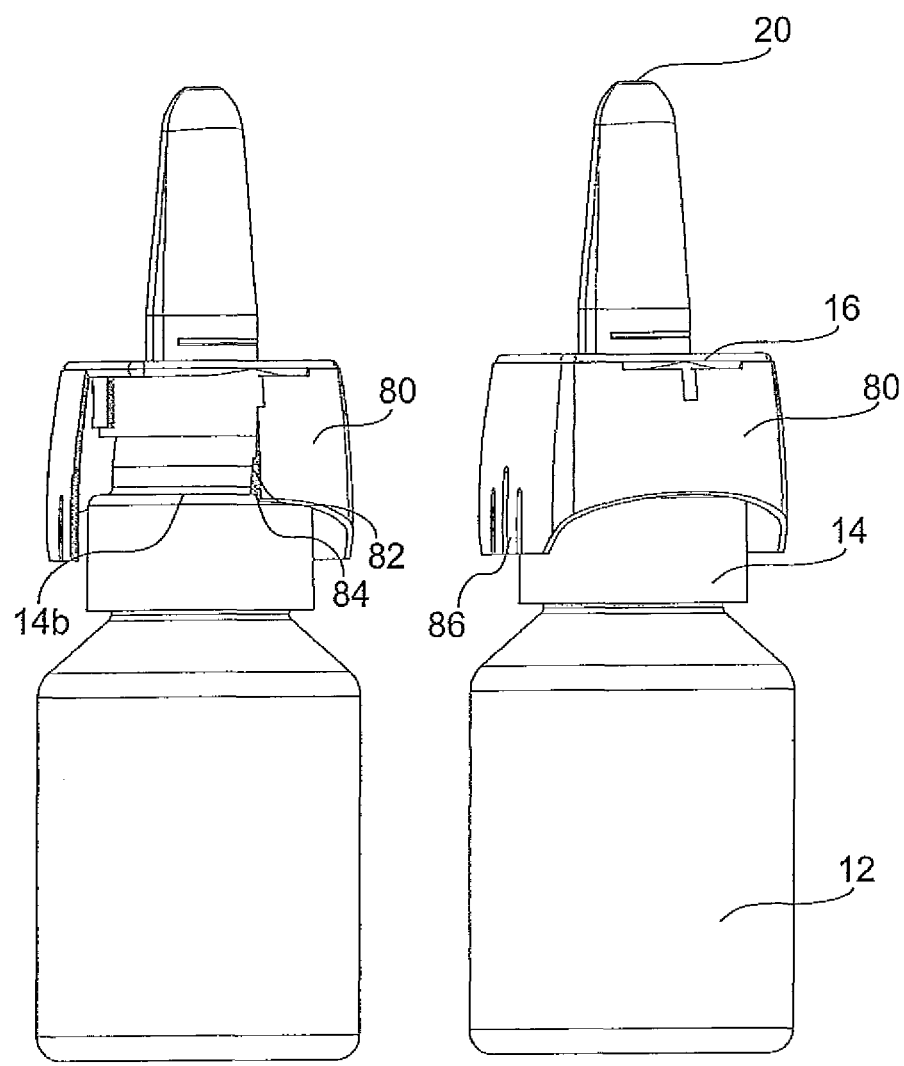
Fig. 7a  Fig. 7b
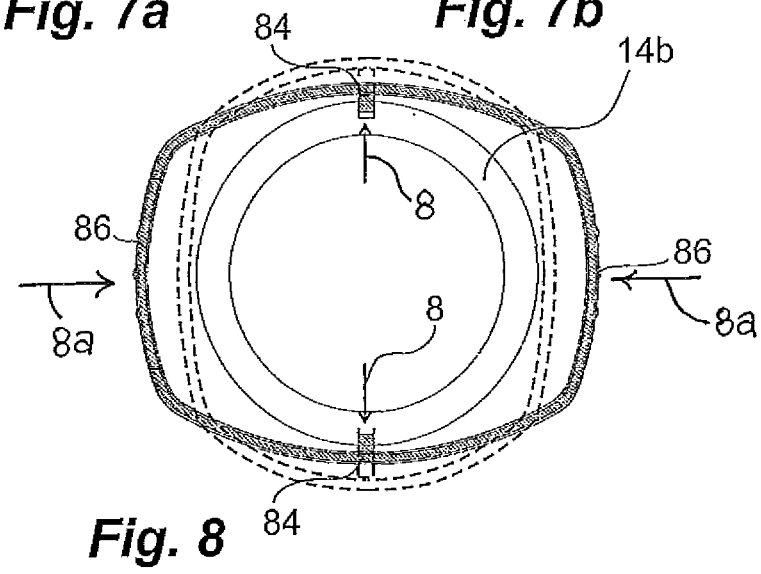
Fig. 8

DISPENSER WITH CHILD-PROOF LOCK

CROSS REFERENCE TO RELATED APPLICATION

This claims priority from German Application No. 10 2012 218 434.1, filed Oct. 10, 2012, the disclosure of which is hereby incorporated by reference in its entirety into this application.

FIELD OF THE INVENTION

The invention relates to a dispenser for discharging a liquid or pulverulent medium comprising a medium reservoir, a discharge opening, and a feeding device for feeding of medium from the medium reservoir to the discharge opening. Therein, such a dispenser has an actuating handle of the feeding device, displaceable relative to the medium reservoir in an actuation direction to thereby effect a discharge of medium.

BACKGROUND OF THE INVENTION

Such dispensers are generally known from the prior art. As an example, reference is made to DE 10 2004 050 679 A1 disclosing a nasal dispenser.

Such dispensers are used for discharging pharmaceutical media. It is often desirable to hinder accessibility of the medium for children so that they may not inadvertently have contact to potentially hazardous media during game-playing.

There are various options for child-proof dispensers known from the prior art. Thus, DE 10 2009 049 903 A1, for example, proposes dispensers that, on the one hand, cannot be actuated with a cap placed-on, since the actuating handle is blocked by the cap. On the other hand, this document features cap designs that can be removed from the respective dispenser only by a sequence of sophisticated moves.

Numerous of the known configurations for child-proof dispensers are related to dispensers that indeed have originally been designed to be child-proof dispensers. However, such child-proof dispensers are comparatively expensive to manufacture, since the partial components thereof are for the most part not adaptable to other possibly non-child-proof dispensers, so that specific tools are required for most of the components of such child-proof dispensers.

SUMMARY OF THE INVENTION

The object of the invention is to provide an alternative to the above-described dispensers, namely configurations of child-proof dispensers that affect the basic structure of the dispenser merely to a minor extent so that the dispenser can be manufactured both as a child-proof dispenser and as a not child-proof dispenser with only minor adaptations.

Said object is achieved according to the invention by three variants.

According to a first variant of the invention, such a dispenser is provided with a protective device or child-proof lock that consists of at least two, and preferably exactly two, partial shells which in a protective condition are connected to one another by at least one coupling device for repeated decoupling and coupling in such a manner that they are immobilized relative to another. Thereby, the protective device is attachable to the feeding device of the dispenser in a protective position such that in the protective condition of the protective device with securely connected partial shells the accessibility and/or maneuverability of the actuating handle is prevented. Only upon releasing the coupling device an enable condition of the protective device is achievable, wherein the partial shells are displaceable relative to another so that the protective device previously surrounding the feeding device is removable from the feeding device, and thus accessibility and/or maneuverability of the actuating handle is obtainable.

Just as with generic dispensers, a dispenser is provided according to the invention which includes a medium reservoir, in which the preferably liquid, however, optionally also pulverulent medium, is present prior to being discharged. The feeding device of such a dispenser connects the medium reservoir to a discharge opening through which the medium can be discharged into a surrounding atmosphere, and thus in particular to body parts of a patient. Said feeding device is operable by means of an actuating handle, wherein the actuating handle is displaceable preferably along a defined, and in particular linear, path relative to the medium reservoir to cause the discharge procedure. An option for configuration of such a feeding device is the configuration of a piston pump capable of driving a partial portion of the medium outwards through the discharge opening by pressure application to the medium.

Preferably, the actuating handle is designed in the type of a finger rest for application of one or two fingers.

The protective device provided according to said first variant of the invention comprises said two partial shells which in the coupled protective condition thereof cause the non-maneuverability or inaccessibility of the actuating handle. For this purpose, the partial shells can surround the feeding device and the actuating handle as a whole in such a manner that before separating the protective device from the feeding device not even the presence of the actuating handle is visible from the outside. In a simplified configuration, the actuating handle is visible with the protective device installed, however, the handle is either not accessible or is blocked by the protective device, preferably by positive locking, such that it cannot be displaced relative to the medium reservoir to a sufficient extent that a significant feeding of medium can be caused thereby. The two partial shells can be coupled to another and decoupled from another repeatedly so that in each case before use of the dispenser, decoupling of the coupling device and removal of the protective device are performed, while after completed use of the dispenser both the partial shells are again coupled to another in the protective position, and thus prevent handling by children.

The protective device is matched to the shape design of the dispenser in such a manner that it cannot be removed without previous decoupling.

In the protective condition of the protective device, wherein the partial shells are immobilized relative to another, said shells form a sleeve open at least on one side, and surrounding the dispenser not more than partially in the vicinity of the feeding device and as the case may be up to the discharge opening. In one configuration, in which the discharge opening is not intended to be surrounded, said sleeve formed by the two partial shells may be open on both sides.

Preferably, the two partial shells of the protective device have about the same size, this means that each of the partial shells surrounds the preferably approximately rotationally symmetric feeding device over an angle of about 180° (+/− 10°). However, configurations other than the above indicated one are conceivable, wherein significantly different sizes are provided, with the smaller of the partial shells surrounding not more than an angular range between 90° and 170°.

It will be appreciated that the configuration is operable with only one coupling device, since the partial shells preferably are not completely separated from another even in the decoupled condition, but merely are maneuverable relative to one another in a defined way. To that effect, in particular a hinge connection, particularly a connection using an integral hinge, may be provided between the partial shells. However, generally, even two completely separate partial shells, and preferably two opposite coupling devices, may be provided which are interconnected only in the protective condition.

In particular, with a configuration of the protective device in which the discharge opening is covered therewith as well, it is difficult for children to comprehend that the protective device has to be removed and that at first a decoupling of the partial shells is required for this purpose. Safety is further increased in particular in that the coupling device is preferably configured such that it is difficult to handle for children.

Preferably, the at least one coupling device comprises two positive fitting coupling portions on the two partial shells which, by sectionally deforming one or both partial shells, the coupling device can be transferred from the coupled to the decoupled condition. For that purpose, it may in particular be required to deflect at least one coupling portion of one or both partial shells in a radial direction.

However, it is considered to be advantageous that at least two separately operable coupling devices are provided on the same side of the protective device that require a more complex relative movement of partial sections of the partial shells for the purpose of decoupling. Thus, on the one hand, by providing deforming coupling portions of both partial devices in the same direction, decouplability may be achieved. This is to mean that in the vicinity of a contact line of the partial shells, there are provided two coupling devices offset one from the other, and each is decoupled by deforming coupling portions provided on the two partial shells in identical directions. As an alternative thereto, two coupling portions may be provided on the same partial shell and displaced in opposite directions to allow decouplability. Thus, one of said partial portions can be movable radially in the direction of the feeding device and the other partial portion can be movable radially away from the feeding device.

Another adequate way for production of a coupling device that is difficult to handle for children is achievable in that the coupling device includes a coupling opening on a partial shell and a coupling prolongation on the other partial shell penetrating the coupling opening in the coupled condition, wherein the coupling prolongation is designed such that for passing through the coupling opening for the purpose of decoupling, said prolongation has to be twisted. It was observed that the twisting movement of the coupling prolongation is a manipulation that is difficult to comprehend for children and demands motor skill abilities too advanced for children.

According to a second variant of the invention, a generic dispenser is provided comprising a protective device which has a main segment and a switch segment. The main segment per se has a base portion and at least one protective arm which is pivotable relative to the base portion. Thereby, the switch segment is displaceable relative to the main segment between a protective position and an enable position. Thereby, the switch segment limits maneuverability of the protective arm of the main segment in the protective position, while in the enable position there is no functional limiting obtained. Said protective device in total is attachable or fixedly attached to the feeding device such that upon securing of the main segment by means of the switch segment, the accessibility and/or maneuverability of the actuating handle relative to the medium reservoir is prevented, and/or the protective device is not removable from the feeding device. In contrast, by displacing the switch segment to the enable position and the thus achievable maneuverability of the protective arm relative to the base segment, accessibility or maneuverability of the actuating handle is obtainable and/or is in total removable from the feeding device according to a configuration of the protective device.

Thus, the protective device provided according to the second variant comprises two main components, namely the main segment and the switch segment. The base portion of the main segment may be attached to the dispenser fixed in position relative to the actuating handle or the medium reservoir. The protective arm which is pivotable in relation thereto may then in a pivoted position, by the ways and means as described, prevent maneuverability or accessibility of the actuating handle by cooperating with the actuating handle or other components of the dispenser. In another pivoted position relative thereto, said prevention is not obtained. By means of the switch segment which is displaceable relative to the main segment of the protective device, the pivotability of the protective arm can be prevented so that said arm is fixed in said position in which it prevents maneuverability or accessibility of the actuating handle or prevents removability of the protective device. What is required is initially displacing the switch segment to subsequently allow pivoting of the protective arm and thereby obtain usability of the dispenser.

Preferably, the switch segment is translationally slideable relative to the base portion of the main segment, wherein said movability is limited preferably in both moving directions by stops on the main portion.

It was observed that it is usually difficult to comprehend for children that at first the switch segment has to be displaced or moved to ensure usability of the dispenser. Thus, the switch segment presents an effective way to provide a child-proof feature.

It is of particular advantage, when the base portion of the main segment is annular, wherein in particular it may be designed such that it rests on the actuating handle in the protective position. The at least one protective arm of the main segment is preferably hinged on the main segment to be pivotable about a tangential axis.

The main segment and the at least one protective arm are preferably formed in one piece and interconnected via an integral hinge.

Particularly advantageous is a design, wherein a plurality of protective arms is provided which are pivotable about differing pivot axes relative to the base portion. The plurality of protective arms, two or three protective arms are preferred, are preferably distributed over the circumference of the base portion.

Particularly advantageous therein is that the maneuverability of the plurality of protective arms is limitable conjointly by the one switch segment. This is achieved in particular in that the switch segment also has an annular design and in the protective position thereof surrounds the plurality of protective arms so that they cannot be deflected outwards and diverge.

Both the first and the second variant of the invention may be configured such that they do not adopt a cap function, but merely restrict maneuverability or accessibility of the actuating handle relative to the medium reservoir in the mentioned manner. However, of particular advantage is in each case a configuration, wherein even the discharge opening is covered by the protective device so that an additional protection is obtained. The said protective devices preferably prevent movement of the actuating handle by positive fitting. In the case of the second variant, this may be achieved, for example, in that on the main segment both for the actuating handle and for components of the dispenser fixed in position to the medium reservoir, for example, a base body of the feeding device, stop surfaces are provided to ensure a defined spacing of the actuating handle from the medium reservoir, as long as the protective arms are retained by the switch segment in their defined protective pivot position.

In a third variant of the invention a generic dispenser is provided which has an advanced configuration in that to the actuating handle is assigned a locking device, which is displaceable relative to the medium reservoir together with the actuating handle. Said locking device can prevent movement of the actuating handle relative to the medium reservoir in a locking condition and permit said movement in an enable condition. To obtain the enable condition, the locking device has two compressible unlocking surfaces opposite to another and orthogonal to the actuation direction, wherein by compressing said unlocking surfaces the locking device is transferable into the enable position thereof.

Preferably, the locking device is configured in a ring surrounding the feeding device at least sectionally, wherein the unlocking surfaces are provided on the exterior of the ring, and wherein at least one stop surface is provided which is offset circumferentially relative to the unlocking surfaces, and which for locking actuation in the locking condition of the locking device abuts on a countersurface fixed in position relative to the medium reservoir. Said stop surface of the locking device may be displaced radially outwards by radial compressing of the unlocking surfaces to be moved away from the region of said countersurface and thus produce the enable condition.

A particular advantage is when the locking device therefor has a one-piece, deformable annular component on which both the unlocking surfaces and the stop surface are provided. The effect of said configuration in an annular component is that by compressing, and causing the unlocking surfaces to approach one another radially, a radial outwards deflection of the stop surface is simultaneously effected.

The locking device may be an integral constituent of the actuating handle and be formed in one piece with the handle. Optionally, with such a configuration it may be an advantage to produce said component constituting the actuating handle and the locking device by two-component injection molding, to ensure sufficient deformability of the locking device.

However, a particularly advantageous configuration is considered in that the locking device is configured in a separate component relative to the actuating handle, which is coupled to the actuating handle by form fitting or force fitting. Thus, the locking device may be mounted as an additional component to a dispenser that for the rest is almost unvaried as compared to conventional dispensers, to ensure the desired child-proof function.

Preferably, for all variants it is provided that all the components described, in particular all components of the protective devices, are synthetic material components.

Since a dispenser according to the invention serves for discharging pharmaceutical liquids, it is preferably filled with such a liquid in the condition as supplied to the customer. In particular the use of a dispenser according to the invention is intended for pharmaceutical liquids, where the risk for children is particularly high. For example, there may be analgetics involved in this case. However, a dispenser according to the invention is appropriate for all other types of liquid and pulverulent medicaments available by prescription.

BRIEF DESCRIPTION OF THE DRAWINGS

Further aspects and advantages of the invention will become apparent from the description below of preferred exemplary embodiments of the invention. The drawings show in:

FIG. 2, the protective device of the dispenser of FIGS. 1a and 1b in the decoupled condition;

FIGS. 3a and 3b, variants of the dispenser of FIGS. 1a, 1b, and 2;

FIGS. 7a and 7b, a dispenser according to a third variant of the invention in a partially sectional view and a non-sectional view; and FIG. 8, a sectional view through the locking device of the dispenser of FIGS. 7a and 7b.

DETAILED DESCRIPTION

Figure 1:
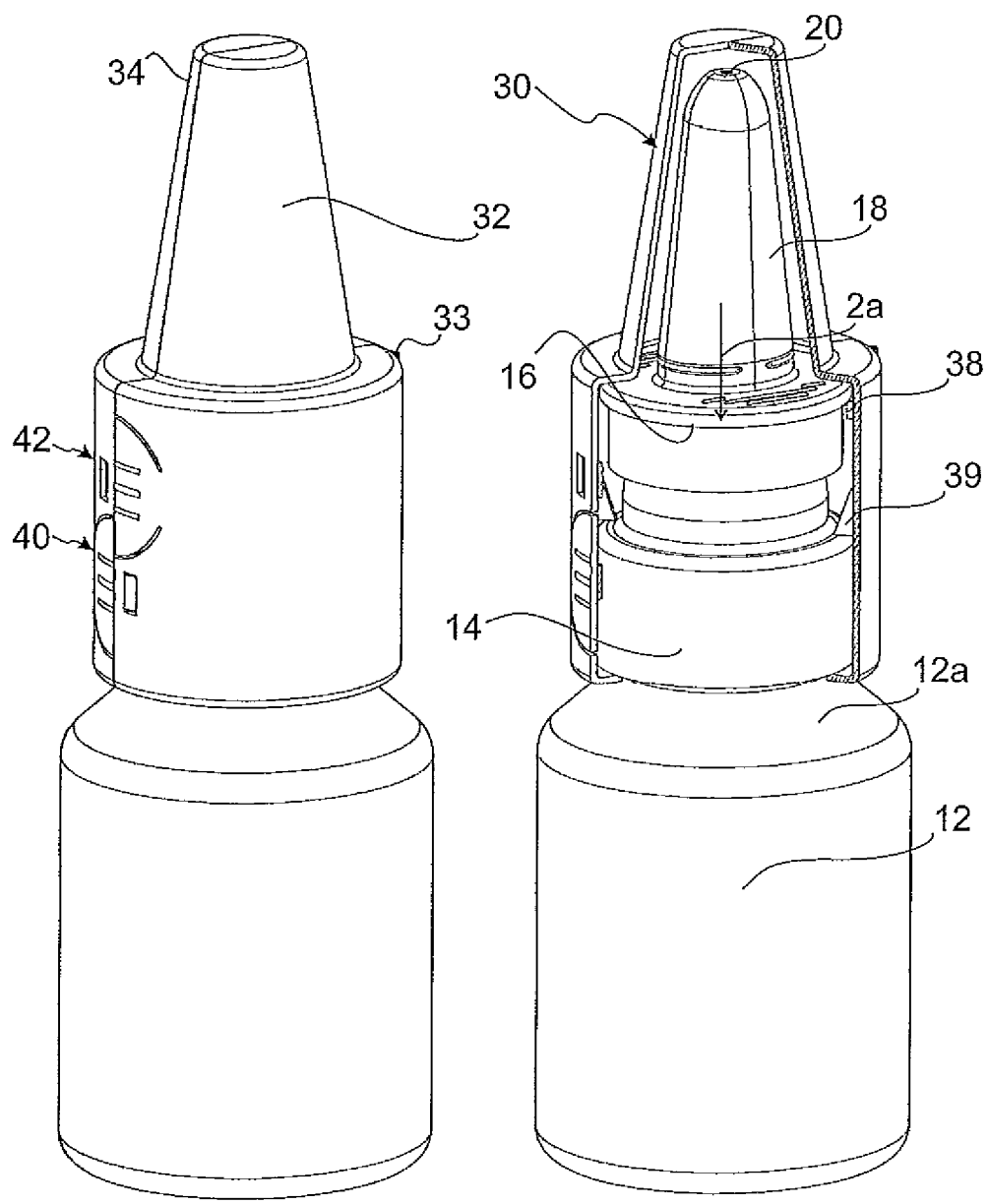
FIGS. 1a and 1b, a dispenser according to a first variant of the invention in a non-sectional and a partially sectional view.

FIGS. 1a and 1b show an embodiment of the first variant of the invention. Referring to the partial sectional view of FIG. 1b, a dispenser is used which is comparable as regards the basic structure thereof to well-known dispensers. Said basic structure comprises a medium reservoir 12, a feeding device 14 attached on a neck 12a of the medium reservoir 12 including an actuating handle 16 for actuating the feeding device 14, and a discharge opening 20 in the present case provided on the distal end of a nose olive 18. By displacement of the actuating handle 16 in the direction of the arrow 2a, a piston pump, not illustrated in detail, provided within the feeding device 14 can be activated to feed liquid medium from the medium reservoir 12 to the discharge opening 20.

To prevent any improper use of the dispenser by children, a protective device 30 is provided. Said protective device 30 includes two partial shells 32, 34 interconnected by an integral hinge 33. In the manner as illustrated in FIG. 2, said integral hinge 33 allows pivoting of the partial shells relative to another to provide the opened condition of the protective device 30. In the closed condition, illustrated in FIGS. 1a and 1b, the partial shells 32, 34 are pivoted by 180° as compared to the condition of FIG. 2, and secured in the closed condition by two coupling devices 40, 42.

The coupling devices 40, 42 are of similar structure, however, the coupling devices differ in regard to distribution thereof on the partial shells 32, 34. In the case of the coupling device 40, a coupling portion 40a elastically deflectable relative to the partial shell 34 is provided with a latch portion 40b on the partial shell 34, while on the other partial shell 32 a recess 40c for the latch portion 40b is provided. In contrast, in the case of the second coupling device 42, the elastically deflectable portion 42a with the latch portion 42b is provided on the partial shell 32, while the corresponding recess 42c is provided on the second partial shell 34.

As a result, said configuration requires that for separating the protective device 30 from the feeding device 14 and the actuating handle 16, both mutually offset coupling portions 40a, 40b have to be pressed down simultaneously. Only when this has been done can the partial shells 33, 34 be pivoted relative to one another to allow their separation from the feeding device 14 and the actuating handle 16, and thus reestablish accessibility to the actuating handle 16. In particular young children have, first of all, difficulty in comprehending that the protective device 30 cannot simply be pulled off, due to the fact that it engages behind a lower rim 36 of the feeding device 14, but instead has to be pivoted open. In addition, in particular young children have difficulty in performing, as regards to the motion sequence, simultaneous pressing of the two decoupling surfaces 40a, 42a and then the required pivoting opening movement.

While the configuration of FIGS. 1a, 1b and 2 provides that not only the feeding device 14 and the actuating handle 16, but also the nose olive 18 and thus also the discharge opening 20 are covered by the protective device, alternative configurations are conceivable as well, wherein the two partial shells 32, 34 in the coupled condition form a common protective sleeve which is open at both ends and with the nose olive 18 extending outwards therefrom. However, in the case of such a configuration, an advantage is when on the interior surface of the partial shells 32, 34 a prolongation 38 is provided, illustrated in dashed lines in FIG. 1b, said prolongation together with prolongations 39, that are equally facing the interior and sitting on a stop surface of the feeding device 14, mechanically preventing displaceability of the actuating handle 16.

FIGS. 3a and 3b show alternative embodiments of the coupling device.

In the embodiment of FIG. 3a, there are as well two coupling devices 140, 142 provided, wherein each of said devices comprises a pivot leg 140a, 142a attached to the partial shell 32 and including recess 140b, 142b. On the other partial shell 34 are provided corresponding cams which in the coupled condition of the partial shells 32, 34 as illustrated are disposed in the recesses 140b, 142b of the pivot legs 140a, 142a. For decoupling, the pivot legs 140a, 142a have to be approached in the direction of the arrows 4.

In the configuration according to FIG. 3b, a coupling device 240 including coupling flanges 241, 242 is provided on the partial shells 32, 34, wherein in the coupling flange 241 a recess 241a is provided, and wherein on the other coupling flange 242 a coupling prolongation 242a including a flared end zone 242b is provided. In the coupled condition of FIG. 3b, the coupling prolongation 242a projects through the coupling perforation 241a. Since the flared end zone 242b in the untwisted condition of the prolongation 242a is wider than the width of the perforation 241a, a reliably coupled condition is achievable thereby. For decoupling, the end zone 242b of the coupling prolongation 242a has to be twisted by about 90°, for the flared end zone 242b to pass through the perforation 241a. Such a torsional move is difficult to realize for children both in regard to comprehension and also in regard to motor skill abilities.

Figure 4:
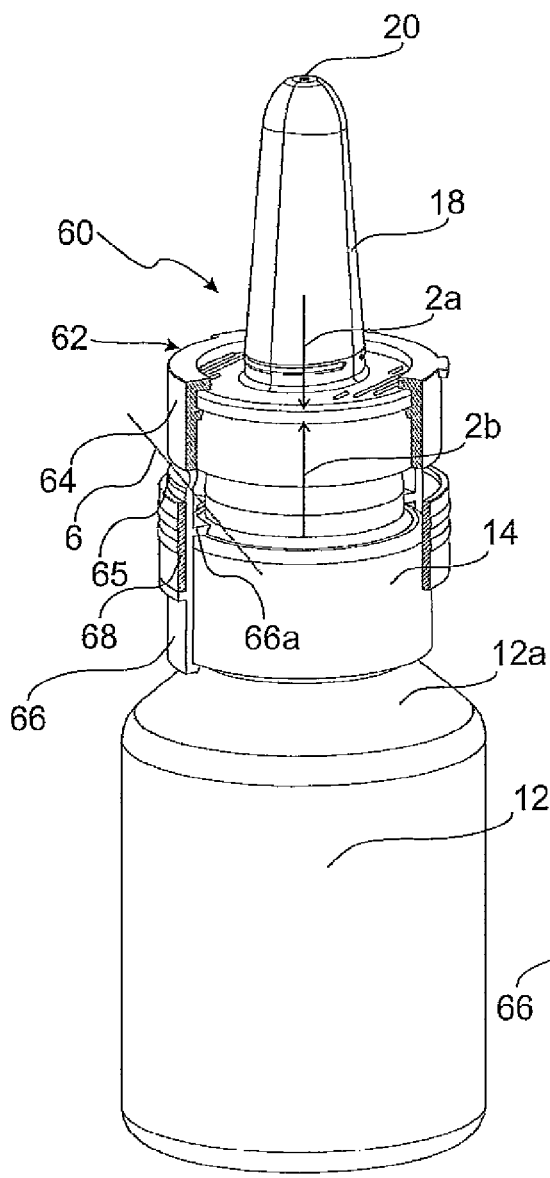
FIGS. 4 and 5, a dispenser according to a second variant of the invention in a partially sectional view of the protective condition of the dispenser and a non-sectional view of the unlocked condition.
Figure 5:
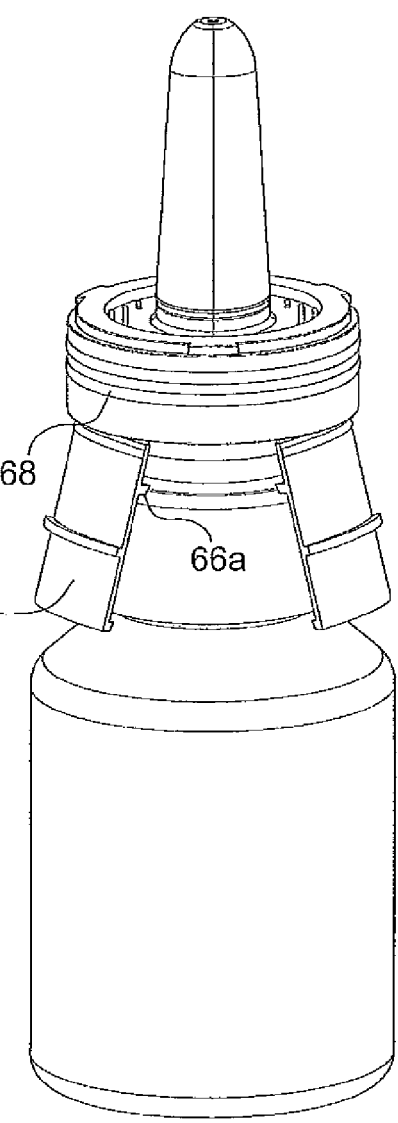

FIGS. 4 and 5 show a dispenser according to a second variant of the invention. The basic structure of said dispenser comprising medium reservoir 12, feeding device 14, actuating handle 16, and nose olive 18 having a discharge opening 20 on the distal end thereof is comparable to the dispenser of the previous figures. However, the protective device 60 according to the dispenser of FIGS. 4 and 5 is of a significantly different type. Said protective device 60 comprises two separate components, namely a main segment 62 and a switch segment 68. The main segment 62 has a base portion 64 fixedly connected to the actuating handle 16, as clearly apparent from FIG. 4. The base portion 64 is annular in shape. On the lower end of the base portion 64, there is a total of three pivotable protective arms 66, each pivoting about tangential axes 6 by means of integral hinges 65 on the base portion 64.

While FIG. 4 shows a protective pivot position of the protective arms 66, FIG. 5 shows an unlocked pivot condition. With reference to FIG. 4, it is readily apparent that on the interior side of the protective arms 66 support surfaces 66a are provided and cooperate with the base body of the feeding device 14 in the protective condition of FIG. 4 in such a manner that displacement of the actuating handle 16, which can be displaced only together with the base portion 64 in the direction of the arrow 2a, is not feasible. Such a movement is permitted only after the protective arms 66 have assumed the position as illustrated in FIG. 5. In the protective condition of FIG. 4 said pivoting is prevented by the switch segment 68. The switch segment 68 is in the shape of a ring which is provided on the exterior of the main segment 62, and is movable between an upper end position in FIG. 5 and a lower end position in FIG. 4. In the lower end position of FIG. 4, the switch segment 68 secures the protective arms 66 and prevents outwards deflection thereof. Initially, it is necessary to displace the switch segment 68 in the direction of the arrow 2b upwards, up to the switch assuming the position of FIG. 5. Only after that the protective arms 66 can be pivoted outwards and subsequently permit an unhindered actuation by displacement of the actuating handle and the entire protective device 60 in the direction of the arrow 2a.

The complex motion sequence is difficult to accomplish at least for young children, in particular since the direction of movement of the switch segment 68 for unlocking the protective device 60 has to be performed in a direction 2b opposite to the actual direction of actuation 2a.

Figure 6:
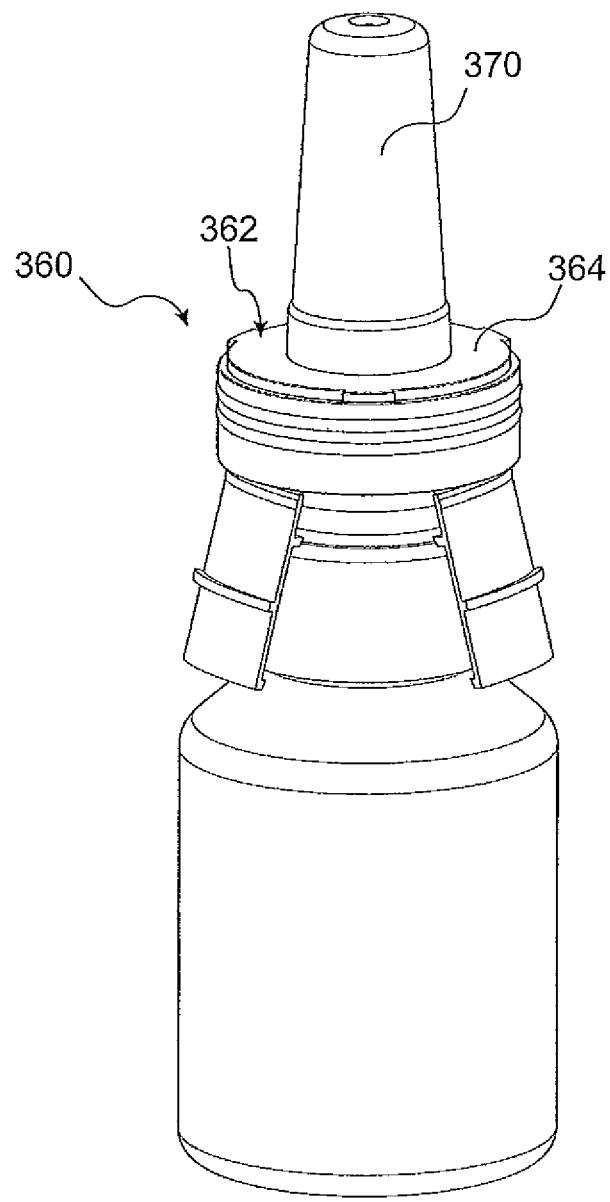
FIG. 6, a variant of the dispenser of FIGS. 4 and 5.

FIG. 6 shows a modification of the embodiment of FIGS. 4 and 5, differing in that herein the base portion 364 of the main segment 362 of the protective device 360 is not fixedly connected to the actuating handle 16. Instead, in the case of the embodiment of FIG. 6, the protective device comprises also a cap portion 370 covering the discharge opening 20. Said configuration provides that after unlocking, in a manner as described in relation to FIGS. 4 and 5, the protective device 360 as a whole unit and including the cap portion 370 is removed, to then permit a discharge procedure.

FIGS. 7a, 7b and 8 show an embodiment of the third variant of the invention. Therein, FIG. 7a shows a partially sectional illustration for explanation. Again, the basic structure of the dispenser exhibits the same features as the previous dispensers, namely a medium reservoir 12 adjoined to a feeding device 14, a respective actuating handle 16, and a nose olive 18 including a discharge opening 20.

The specific feature of the embodiment according to FIGS. 7a, 7b and 8 is in a locking device 80 attached to the actuating handle 16. Said locking device 80 has an annular structure, as apparent from FIG. 7a, with a latch 82 having a stop surface 84 provided on the interior surface thereof. As apparent from the sectional view of FIG. 8, said latch 82 and the stop surface 84 cover a stop surface 14b of the feeding device 14 in the locked initial condition of the locking device 80. As a result, pressing down the actuating handle 16 is not possible.

To effect a discharge procedure by pressing down the actuating handle 16 in the direction of the arrow 2a, the locking device 80 needs to be deformed. For that purpose, unlocking surfaces 86 are provided on opposite sides of the exterior surface of the locking device 80. By applying force to said unlocking surfaces, deforming of the locking device 80 is caused, as illustrated in dashed lines in FIG. 8. The movement of the unlocking surfaces 86 in directions 8a approaching one another simultaneously results in a diverging movement of the latches 82 in the direction of the arrows 8. Thereby, the latches 82 are displaced sufficiently far outwards so that a subsequent pressing down of the actuating handle 16 is permitted.

Although the conception of said locking device is very simple, it is very difficult to handle for children. In particular this is due to the fact that at least young children would need both hands to press the locking surfaces 86 to make them approach one another. However, they would not succeed, upon unlocking achieved in such a manner, to press down the actuating handle 16 together with the locking device 80, to the effect that a discharge procedure is not accomplished.

The invention claimed is:

1. A dispenser for discharging a liquid or pulverulent medium comprising
   a medium reservoir;
   a discharge opening;
   a feeding device for feeding of medium from the medium reservoir to the discharge opening, the feeding device comprising an actuating handle displaceable relative to the medium reservoir in an actuation direction by which the feeding device is actuated for discharge;
   a protective device including two partial shells connectable to one another in a protective condition by at least one coupling device for repeated decoupling of the partial shells and coupling of the partial shells such that the partial shells when coupled are immobilized relative to one another and are in the protective condition, the coupling device including positive fitting coupling portions on the partial shells, the coupling portions being transferable from a coupled into a decoupled condition by deforming the coupling portion of one partial shell or by deforming the coupling portions of both partial shells, the protective device being attachable to the feeding device of the dispenser in a protective position and being configured such that the protective device, when in the protective condition and attached to the feeding device in the protective position, the accessibility and/or maneuverability of the actuating handle is prevented and the protective device covers the discharge opening, and upon releasing the coupling device an enable condition of the protective device is achieved in which the partial shells are displaced relative to one another so that the protective device is removed in its entirety from the feeding device to allow access to and/or maneuverability of the actuating handle.

2. The dispenser according to claim 1, wherein the two partial shells are pivotably interconnected by a hinge.

3. The dispenser according to claim 1, wherein one of the coupling portions of the coupling device comprises a coupling opening on one partial shell and the other of the coupling portions comprises a coupling prolongation on the other partial shell penetrating the coupling opening in the coupled condition, wherein the coupling prolongation is deformed by twisting to permit the coupling prolongation to pass through the coupling opening to achieve the decoupled condition.

4. The dispenser according to claim 1, wherein the protective device is only fixedly attached to the feeding device when in the protective condition and upon transfer of the coupling portions to the decoupled condition the partial shells are displaced in respective directions away from one another and the protective device in its entirety detaches from the feeding device.

5. The dispenser according to claim 4, wherein the protective device, when in the protective condition and attached to the feeding device in the protective position, wholly encloses the feeding device and the discharge opening.

6. The dispenser according to claim 1, wherein the at least one coupling device includes two separately operable coupling devices, the two separately operable coupling devices being first and second coupling devices and the coupling portions being first and second coupling portions, the first coupling portion forming part of the first coupling device and the second coupling portion forming part of the second coupling device, the first coupling device being disposed on one of the partial shells and the second coupling device being disposed on the other of the partial shells, and the enable condition is achieved by deforming the first and second coupling portions in the same direction.

7. The dispenser according to claim 1, wherein the at least one coupling device includes two separately operable coupling devices, the two separately operable coupling devices being first and second coupling devices and the coupling portions being first and second coupling portions, the first and second coupling portions forming part of the first coupling device and the second coupling device including third and fourth positive fitting coupling portions, and the enable condition is achieved by deforming the first coupling portion and the third coupling portion in opposite directions from one another.

8. The dispenser according to claim 7, wherein the first and third coupling portions are pivotably deformable in opposite directions from one another to release the first and third coupling portions from the respective said second and fourth coupling portions, and the first and third coupling portions are disposed on one of the partial shells and the second and fourth coupling portions are disposed on the other of the partial shells.

9. The dispenser according to claim 2, wherein said hinge is oriented substantially parallel to a longitudinal axis of said dispenser.

10. A dispenser for discharging a liquid or pulverulent medium, said dispenser comprising:
    a medium reservoir;
    a discharge opening;
    a feeding device including a handle mounted for displacement relative to said medium reservoir in an actuation direction, wherein displacement of said handle in the actuation direction activates said feeding device to cause said feeding device to feed medium from said medium reservoir to said discharge opening; and
    a protective device including first and second partial shells and a coupling arrangement, said first and second partial shells being connected to one another for repeated movement between a protective closed configuration in which said coupling arrangement maintains said first and second shells substantially non-movable relative to one another, and an enabling open configuration in which said coupling arrangement is released and said first and second partial shells are displaced away from one another, said protective device in the protective closed configuration being attached to said feeding device such that said first and second partial shells cover said discharge opening and block access to, or prevent maneuverability of, said handle, and said protective device and said first and second partial shells in the enabling open configuration being wholly separated from, and unattached to, said feeding device to allow access to, or allow maneuverability of, said handle.

11. The dispenser according to claim 10, wherein said protective device is only fixedly attached to said feeding device in the protective closed configuration and upon release of said coupling arrangement said first and second partial shells are displaced in respective directions away from one another and said protective device in its entirety detaches from said feeding device.

12. The dispenser according to claim 10, wherein said first and second partial shells are pivotably connected to one another by a hinge oriented substantially parallel to a longitudinal axis of said dispenser.

13. The dispenser according to claim 10, wherein said first and second partial shells when in the protective closed configuration wholly enclose said feeding device and said discharge opening.

14. The dispenser according to claim 10, wherein said coupling arrangement includes first and second coupling elements respectively disposed on said first and second partial shells, wherein one of said first and second coupling elements is deformed to decouple said first and second partial shells from one another and transfer said protective device into the enabling open configuration.

15. The dispenser according to claim 14, wherein both of said first and second coupling elements are deformed to decouple said first and second partial shells from one another and transfer said protective device into the enabling open configuration.

16. The dispenser according to claim 14, wherein said first coupling element includes an opening defined in said first partial shell and said second coupling element comprises a projection disposed on said second partial shell, said projection being engaged within said opening to couple said first and second partial shells to one another in said protective closed configuration of said protective device, said projection being deformed to release said projection from said opening and decouple said first and second partial shells from one another and transfer said protective device into said enabling open configuration.

17. The dispenser according to claim 16, wherein said first coupling element includes a first flange defining said opening therein and said second coupling element includes a second flange disposed in opposed relation with said first flange and mounting said projection thereon, said projection being deformed by twisting to release said projection from said opening to decouple said first and second partial shells from one another and transfer said protective device into said enabling open configuration.

18. The dispenser according to claim 10, wherein said coupling arrangement includes first and second coupling elements pivotably mounted on said first partial shell, said first and second coupling elements being engaged with said second partial shell to couple said first and second partial shells to one another in said protective closed configuration of said protective device, said first and second coupling elements being pivotably movable in opposite directions to release said first and second coupling elements from said second partial shell and decouple said first and second partial shells from one another and transfer said protective device into said enabling open configuration.

\* \* \* \* \*